United States Patent
Chen et al.

(10) Patent No.: US 10,542,995 B2
(45) Date of Patent: Jan. 28, 2020

(54) VASO-OCCLUSIVE DEVICE

(71) Applicant: Boston Scientific Scimed, Inc., Maple Grove, MN (US)

(72) Inventors: Hancun Chen, San Ramon, CA (US); Richard Murphy, Sunnyvale, CA (US); Jimmy Dao, San Jose, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 626 days.

(21) Appl. No.: 14/941,613

(22) Filed: Nov. 15, 2015

(65) Prior Publication Data
US 2016/0066924 A1    Mar. 10, 2016

Related U.S. Application Data

(63) Continuation of application No. 13/271,453, filed on Oct. 12, 2011, now Pat. No. 9,186,149.
(Continued)

(51) Int. Cl.
*A61B 17/12*    (2006.01)

(52) U.S. Cl.
CPC .... *A61B 17/12145* (2013.01); *A61B 17/1215* (2013.01); *A61B 17/1219* (2013.01); *A61B 17/12031* (2013.01); *A61B 17/12109* (2013.01); *A61B 2017/12054* (2013.01); *A61B 2017/12063* (2013.01)

(58) Field of Classification Search
CPC ........ A61B 17/12145; A61B 17/12031; A61B 17/12109; A61B 17/1219; A61B 17/1215; A61B 2017/12054; A61B 2017/12063
See application file for complete search history.

(56) References Cited

U.S. PATENT DOCUMENTS 5,984,929 A * 11/1999 Bashiri ............ A61B 17/12022
                                                           606/108
9,993,252 B2 * 6/2018 Keeley ............ A61B 17/12022
(Continued)

*Primary Examiner* — Julie A Szpira

(57) ABSTRACT

A vaso-occlusive device includes an inner coil made from inner coil wire having a first diameter and formed from a first material, and an outer coil disposed at least partially around the inner coil and made from outer coil wire having a second diameter and formed from a second material. The inner coil has a first pitch and the outer coil has a second pitch. The first diameter, material, and pitch are different from the second diameter, material, and pitch, respectively. In some embodiments, the second diameter is less than the first diameter, the second material is softer than the first material, and the second pitch is more open than the first pitch. In some embodiments, the inner coil extends proximally beyond the outer coil. In one embodiment, a vaso-occlusive device includes an outer coil defining a lumen and an inner coil disposed at least partially in the lumen, wherein the vaso-occlusive device also includes an intermediate layer disposed between the inner coil and the outer coil, wherein the intermediate layer includes a biocompatible metal or a biocompatible, swellable polymer. The vaso-occlusive device may also include a biodegradable coating disposed on the outer surface of the inner coil. In one embodiment, a vaso-occlusive device includes an outer coil and a plurality of inner coils of increasing size each disposed immediately inside of the outer coil or one of the inner coils.

18 Claims, 9 Drawing Sheets

Related U.S. Application Data

(60) Provisional application No. 61/392,434, filed on Oct. 12, 2010.

(56) References Cited

U.S. PATENT DOCUMENTS

| | | | |
|---|---|---|---|
| 2004/0006363 A1* | 1/2004 | Schaefer .......... | A61B 17/12022 606/200 |
| 2005/0171572 A1* | 8/2005 | Martinez .......... | A61B 17/12022 606/200 |
| 2006/0052823 A1* | 3/2006 | Mirizzi ............ | A61B 17/12022 606/214 |

\* cited by examiner

VASO-OCCLUSIVE DEVICE

RELATED APPLICATION DATA

The present application is a continuation of U.S. patent application Ser. No. 13/271,453, filed Oct. 12, 2011, now U.S. Pat. No. 9,186,149, and claims the benefit under 35 U.S.C. § 119 to U.S. provisional patent application Ser. No. 61/392,434, filed Oct. 12, 2010. The foregoing application is hereby incorporated by reference into the present application in its entirety

FIELD

The field of the disclosed inventions generally relates to vaso-occlusive devices for establishing an embolus or vascular occlusion in a vessel of a human or veterinary patient. More particularly, the disclosed inventions relate to dual layer vaso-occlusive devices.

BACKGROUND

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference, describes a vaso-occlusive device that assumes a linear, helical primary shape when stretched for placement through the lumen of a delivery catheter, and a folded, convoluted secondary shape when released from the delivery catheter and deposited in the vasculature.

In order to deliver the vaso-occlusive devices to a desired site in the vasculature, e.g., within an aneurysmal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 26°, "J", "S", or other bending shape, depending on the particular anatomy of the patient, so that it will stay in a desired position for releasing one or more vaso-occlusive device(s) into the aneurysm once the guidewire is withdrawn. A delivery or "pusher" wire is then passed through the micro-catheter, until a vaso-occlusive device coupled to a distal end of the delivery wire is extended out of the distal end opening of the micro-catheter and into the aneurysm. The vaso-occlusive device is then released or "detached" from the end delivery wire, and the delivery wire is withdrawn back through the catheter. Depending on the particular needs of the patient, one or more additional occlusive devices may be pushed through the catheter and released at the same site.

One well-known way to release a vaso-occlusive device from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied through an electrical contact to the conductive pusher wire completes an electrolytic detachment circuit with a return electrode, and the detachment zone disintegrates due to electrolysis.

Perceived problems with current vaso-occlusive devices include insufficient coil mass per length requiring longer procedure time to feed lengths of coil into the aneurysm during packing of the aneurysm. Perceived problems when using thicker coil wire having a larger outer diameter, e.g. 0.003 to 0.004 inch, to increase coil mass include increased coil stiffness, which leads to the bending of the microcatheter and breaking of the coil during packing. Perceived problems also include the thicker coil wire vaso-occlusive device not being able to bend properly within the aneurysm.

SUMMARY

In one embodiment of the disclosed inventions, a vaso-occlusive device includes an inner coil made from inner coil wire having a first diameter, and an outer coil disposed at least partially around the inner coil and made from outer coil wire having a second diameter, where the first diameter is different from the second diameter. In some embodiments, the second diameter is less than the first diameter.

In another embodiment of the disclosed inventions, a vaso-occlusive device includes an inner coil made from inner coil wire having a first diameter and formed from a first material, and an outer coil disposed at least partially around the inner coil and made from outer coil wire having a second diameter and formed from a second material. In such embodiment, the first diameter is different from the second diameter, and the first material is different from the second material. In some embodiments, the second diameter is less than the first diameter, and the second material is softer than the first material.

In yet another embodiment of the disclosed inventions, a vaso-occlusive device includes an inner coil having a first pitch and made from inner coil wire having a first diameter, and an outer coil disposed at least partially around the inner coil, having a second pitch and made from outer coil wire having a second diameter. In such embodiments, the first diameter is different from the second diameter and the first pitch is different from the second pitch. In some embodiments, the second diameter is less than the first diameter and the second pitch is more open than the first pitch.

In still another embodiment of the disclosed inventions, a vaso-occlusive device includes an inner coil made from inner coil wire having a first diameter and formed from a first material, and an outer coil disposed at least partially around the inner coil and made from outer coil wire having a second diameter and formed from a second material. The inner coil has a first pitch and the outer coil has a second pitch. The first diameter, material, and pitch are different from the second diameter, material, and pitch, respectively. In some embodiments, the second diameter is less than the first diameter, the second material is softer than the first material, and the second pitch is more open than the first pitch. In some embodiments, the inner coil extends proximally beyond the outer coil.

In yet another embodiment of the disclosed inventions, a vaso-occlusive device includes an inner coil having a first pitch and made from inner coil wire of a first material, and an outer coil having a second pitch and made from outer coil wire of a second material. The first pitch is different from the second pitch and wherein the first material is different from the second material. In some embodiments, the second material is softer than the first material, and the second pitch is more open than the first pitch.

In still another embodiment of the disclosed inventions, a vaso-occlusive device includes an outer coil defining a lumen and an inner coil disposed at least partially in the lumen. In some such embodiments, the vaso-occlusive device further includes an intermediate layer disposed between the inner coil and the outer coil, wherein the intermediate layer may comprise or include a biocompatible metal or a biocompatible, swellable polymer. In other embodiments, the vaso-occlusive device includes a biodegradable coating disposed on the outer surface of the inner coil. In some of those embodiments, the biodegradable coating includes PGLA. In still other embodiments, the vaso-occlusive device also includes at least one additional inner coil disposed inside of the lumen.

In yet another embodiment of the disclosed inventions, a vaso-occlusive device includes an outer coil and a plurality of inner coils of increasing size each disposed immediately inside of the outer coil or one of the inner coils.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DETAILED DESCRIPTION OF THE ILLUSTRATED EMBODIMENTS

Figure 1:
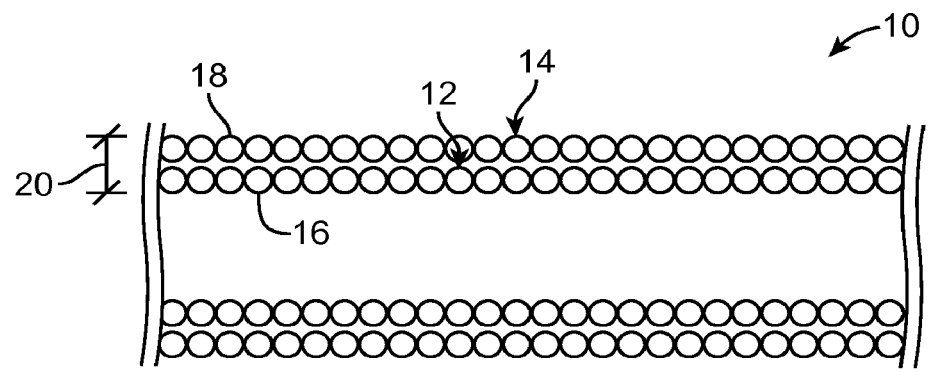
FIGS. 1-9 and 14-16 are detailed longitudinal cross-section views of vaso-occlusive devices according to various embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a vaso-occlusive device 10 in accordance with one embodiment. The vaso-occlusive device 10 includes an inner coil 12 and an outer coil 14. The inner coil 12 has a plurality of loops, and the outer coil 14 is disposed around the inner coil 12. In the embodiment shown in FIG. 1, the inner coil 12 and the outer coil 14 are made from the same material. For example, the inner and outer coils 12, 14 may be made from a metal, such as pure platinum. In other embodiments, the coils 12, 14 may be made from an alloy, such as platinum-tungsten alloy, e.g., 8% tungsten and the remainder platinum. In further embodiments, the coils 12, 14 may be made from any material (e.g., metal, alloy, or a non-metallic material) as long as they are biocompatible. In the illustrated embodiments, the inner coil wire 16 from which the inner coil 12 is made and the outer coil wire 18 from which the outer coil 14 is made have the same cross-sectional dimension. In other embodiments, the wires 16, 18 that form the respective coils 12, 14 may have different cross-sectional dimensions.

It should be appreciated that the vaso-occlusive device 10 of FIG. 1 is advantageous because forming the vaso-occlusive device 10 using two coils 12, 14 may provide a softer, i.e. less stiff, vaso-occlusive device 10 for a given mass per length. In particular, the vaso-occlusive device 10 formed by the two coils 12, 14 with a combined thickness 20 will be more flexible compared to a vaso-occlusive device formed from a single wire having a cross-sectional dimension 20, and formed from the same material as that of the coils 12, 14. In other words, for a given thickness 20 of a wall of the vaso-occlusive device 10, and a given material, formed the vaso-occlusive device 10 using two coils 12, 14 will achieve a softer vaso-occlusive device than that formed using a single coil. This is because a single wire with a cross-sectional dimension 20 will provide a cross-sectional property (e.g., moment of inertia, or bending stiffness) that is higher than the cross-sectional property of the combined two wires 16, 18. Also, when the vaso-occlusive device 10 undergoes bending, part(s) of the inner coil 12 along the length of the inner coil 12 will be allowed to move (e.g., slide longitudinally) relative to the outer coil 14, thereby allowing the vaso-occlusive device 10 to more easily bend.

Figure 2:
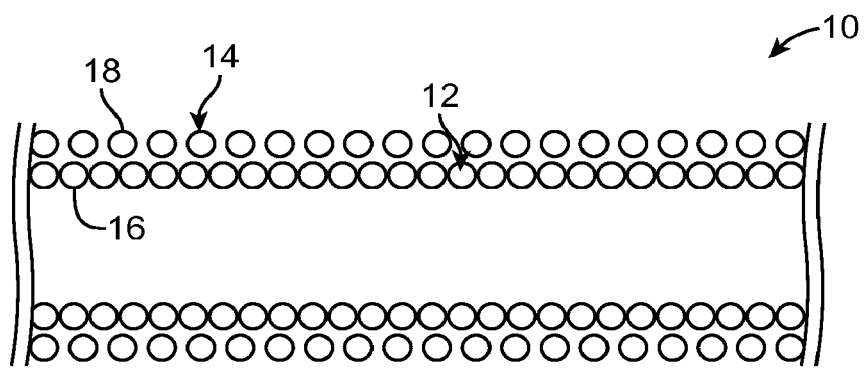

FIG. 2 illustrates a variation of the vaso-occlusive device 10 of FIG. 1. In particular, the vaso-occlusive device is the same as that shown in FIG. 1, except that the outer coil 14 has loops that are more spaced apart than that of the inner coil 12. As shown in FIG. 2, the inner coil 12 has a closed pitch, and the outer coil 14 has an open pitch. Such a configuration may provide further softness for the vaso-occlusive device 10. In other embodiments, the inner coil 12 may also have an open pitch. In such embodiments, the outer coil 14 may have an open pitch that is more open than that of the inner coil 12.

Figure 3:
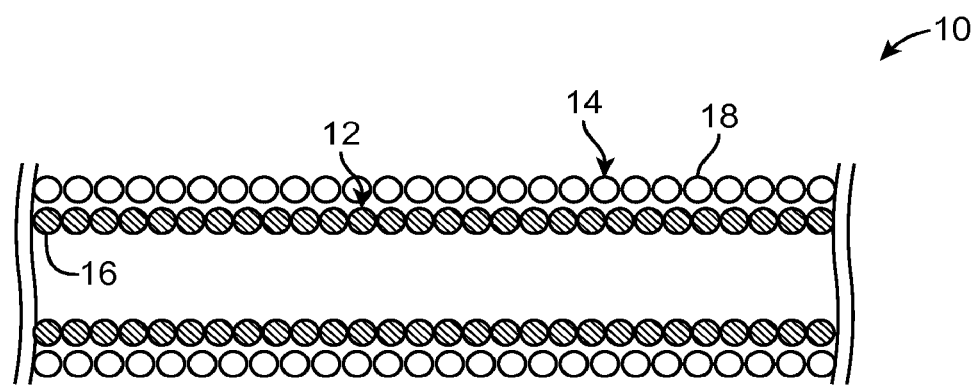

In other embodiments, the inner coil 12 may have a pitch that is more open than that of the outer coil 14. For example, in some embodiments, the outer coil 14 may have a closed pitch, and the inner coil 12 may have an open pitch. Such configuration provides a vaso-occlusive device 10 that has a substantially continuous outer surface formed by the loops of the outer coil 14. In still other embodiments, the inner and outer coils 12, 14 in the devices 10 of FIGS. 1 and 2 may be made from different materials. For example, as shown in FIG. 3, in other embodiments, the outer coil 14 may be made from a metal, such as pure platinum, and the inner coil 12 may be made from an alloy, such as platinum-tungsten alloy, e.g., 8% tungsten and the remainder platinum. In yet other embodiments, the outer coil 14 may be made from an alloy, or a non-metallic material. Also, in other embodiments, the inner coil 12 may be made from a metal or a non-metallic material. By selecting different materials for constructing the coils 12, 14, a desired stiffness may be accomplished for the vaso-occlusive device 10.

Figure 4:
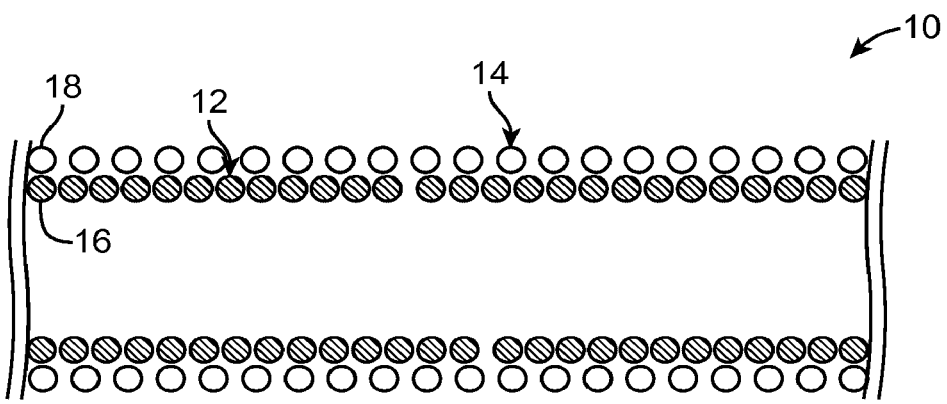

FIG. 4 illustrates a variation of the vaso-occlusive device 10, in which the outer coil 14 of the vaso-occlusive device 10 has loops that are more spaced apart than that of the inner coil 12. As shown in the illustrated embodiments, the inner coil 12 has a closed pitch, and the outer coil 14 has an open pitch. Such configuration may provide further softness for the vaso-occlusive device 10. In other embodiments, the inner coil 12 may also have an open pitch. In such embodiments, the outer coil 14 may have an open pitch that is more open than that of the inner coil 12. In alternate embodiments, the inner coil 12 may have a pitch that is more open than that of the outer coil 14. For example, in other embodiments, the outer coil 14 may have a closed pitch, and the inner coil 12 may have an open pitch. Such configuration provides a vaso-occlusive device 10 that has a substantially continuous outer surface formed by the loops of the outer coil 14.

Figure 5:
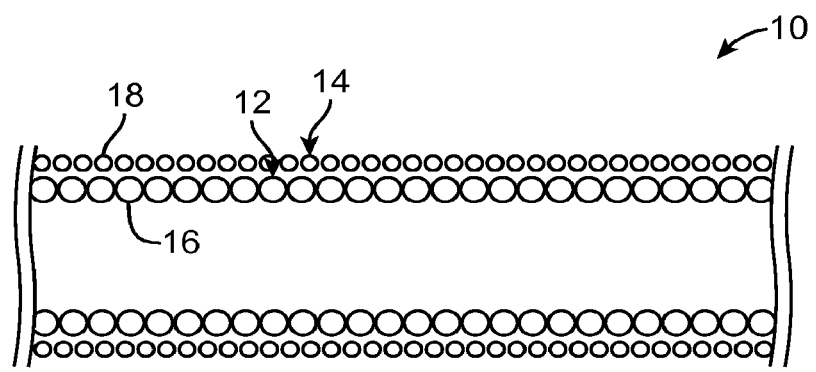

FIG. 5 illustrates a variation of the vaso-occlusive device 10, in which the outer coil 14 is made from outer coil wire 18 that is smaller in diameter than the inner coil wire 16 from which the inner coil 12 is made. Such configuration may provide further softness for the vaso-occlusive device 10.

Figure 6:
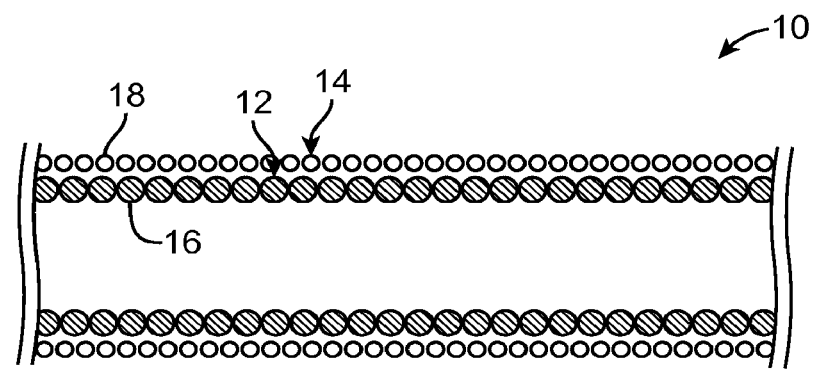

In the embodiment shown in FIG. 6, in addition to the outer coil wire 18 having a smaller diameter than inner coil wire 16, the outer coil wires 18 may be made of different materials than the inner coil wire 16. Making the outer coil wire 18 from softer material than the inner coil wire 16 may provide further softness for the vaso-occlusive device 10.

Figure 7:
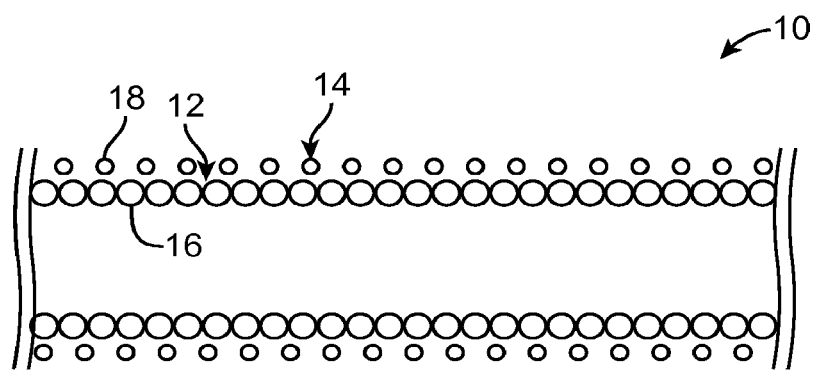

In the embodiment depicted in FIG. 7, the outer coil 14 has an open pitch in addition to being made from outer coil wire 18 having a smaller diameter than inner coil wire 16. In such embodiments, the outer coil 14 may have an open pitch that is more open than that of the inner coil 12. The open pitch of the outer coil 14 may provide additional softness for the vaso-occlusive device 10.

Figure 8:
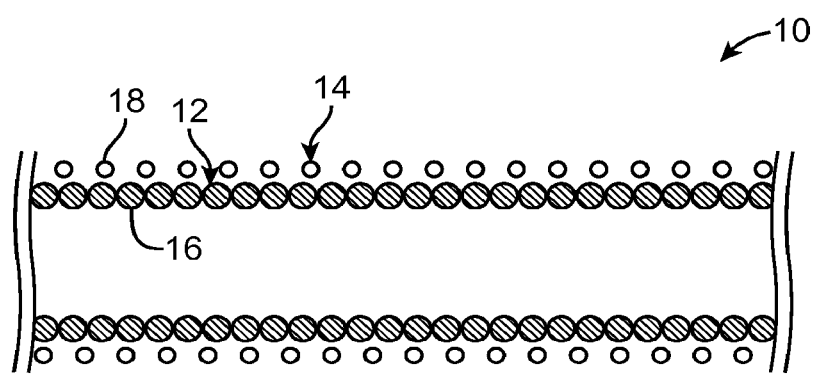

In the embodiment shown in FIG. 8, the outer coil wire 18 has a smaller diameter and is made from softer material than inner coil wire 16, and the outer coil 14 has a more open pitch than the inner coil. These features may combine to provide increased softness for the vaso-occlusive device 10.

Figure 9:
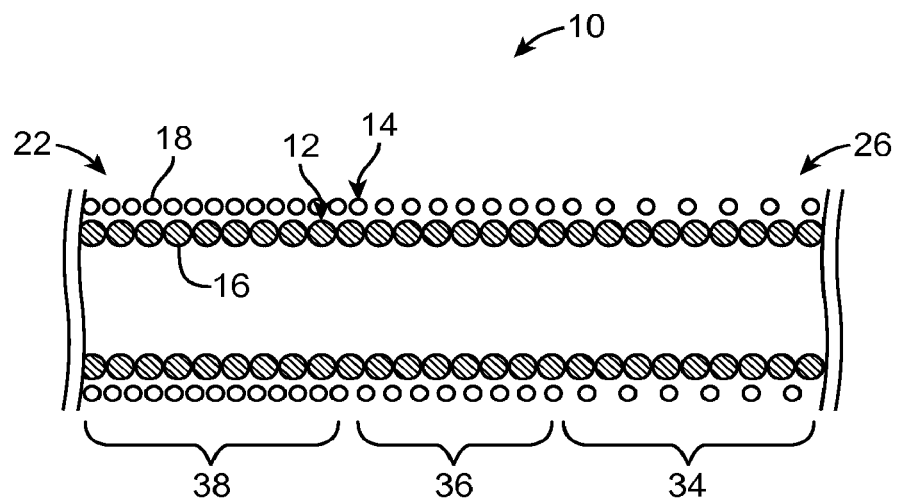

In any of the embodiments described herein, the vaso-occlusive device 10 may have coil windings with different degrees of pitch along the length of the respective coils 12, 14. For example, as shown in FIG. 9, the outer coil 14 may have a closed pitch at a distal section 38, an open pitch at an intermediate section 36, and a more open pitch at a proximal section 34. Such configuration provides a variable stiffness along the length of the vaso-occlusive device 10, wherein the distal end 22 is stiffer than the proximal end 26 of the vaso-occlusive device 10. In the configuration shown, the stiffer distal end 22 allows the vaso-occlusive device 10 to better anchor against the wall of an aneurysm. On the other hand, the softer proximal end 26 improves the coil softness, which may be better for packing inside the aneurysm because the proximal end 26 may be bent more easily.

In other embodiments, instead of having three sections of windings with corresponding three different pitches, the coils 12, 14 may have more than three sections with more than three different pitches, or may have less than three sections with less than three different pitches. In further embodiments, the variability of the pitch along the length of the vaso-occlusive device 10 may be gradual.

Regarding the above-described embodiments of FIGS. 1-9, the wire used for the outer coil may alternatively be made from a pure platinum or platinum-tungsten alloy, and the wire for the inner coil may alternatively be made of a material consisting of a platinum core with an outer layer of platinum-tungsten alloy, or from a material consisting of a core of platinum-tungsten alloy and an outer layer of platinum. More alternatively, the wire for the outer coil can be made from a material consisting of a platinum core and an outer layer of platinum-tungsten alloy, or from a material consisting of a platinum-tungsten core and an outer layer of pure platinum, while the wire for inner coil can be made from pure platinum or platinum-tungsten alloy. Furthermore, the respective outer and inner coils of embodiments of the presently disclosed inventions can alternatively be made of a polymer, a ceramic, a bioactive material, or a combination of such materials. For example, a bioactive coating may be applied to one or both of the outer and inner metallic, polymeric and/or ceramic coils.

Further, while the above-described embodiments of FIGS. 1-9 are directed to double-coil embodiments, i.e., having an outer coil layer and an inner coil layer, it should be appreciated by those skilled in the art that one or more additional coil layers may be included in alternative embodiments for a total of three or more coil layers, in accordance with the inventive aspects disclosed herein. Such three-or-more coil layer embodiments would comprise an outer coil layer, and two or more inner coil layers.

Figure 10:
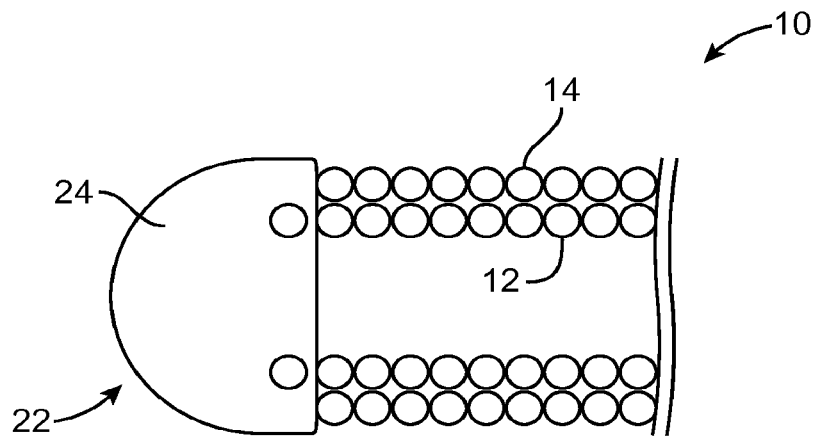
FIGS. 10 & 11 are detailed longitudinal cross-section views of the distal ends of vaso-occlusive devices according to two embodiments.
Figure 11:
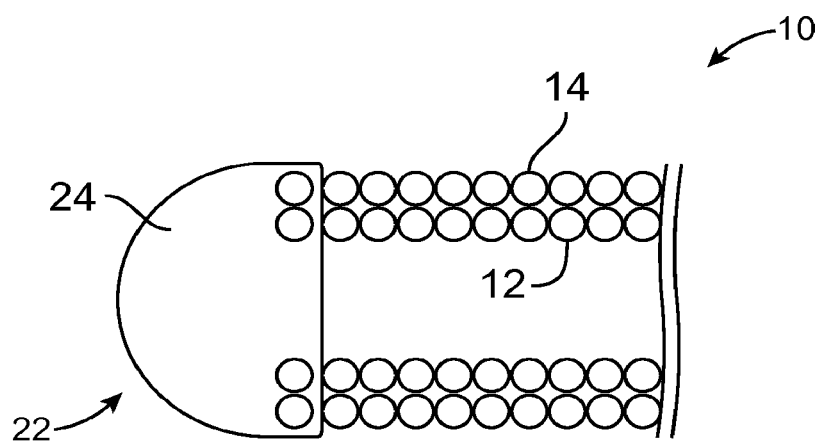

FIG. 10 illustrates a distal end 22 of the vaso-occlusive device 10 in accordance with some alternate embodiments, wherein the vaso-occlusive device 10 may be any of the vaso-occlusive devices 10 shown and described with reference to FIGS. 1-9. As shown in FIG. 10, the end of the inner coil 12 is fixedly attached to a blunt tip 24. In particular, the end of the inner coil 12 is embedded within the blunt tip 24. The attachment of the coil 12 to the blunt tip 24 may alternatively be accomplished using a weld, glue, screw threads, or other suitable adhesive. In the illustrated embodiments, the outer coil 14 is coupled to the inner coil 12 by friction, and is not directly attached to the blunt tip 24. In other embodiments, the outer coil 14 may be directly secured to the inner coil 12 using a weld, glue, or a suitable adhesive. For example, the outer coil 14 may be welded to the inner coil 12 at one or both ends of the coil 14. In further embodiments, in addition to, or instead of, securing to the inner coil 12, the outer coil 14 may be directly attached to the blunt tip 24 (FIG. 11).

Figure 12:
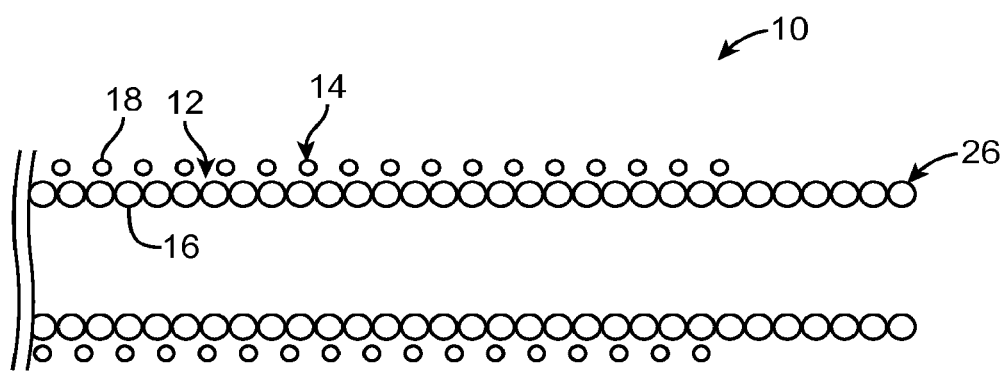
FIG. 12 is a detailed longitudinal cross-section view of the proximal end of a vaso-occlusive device according to one embodiment.

FIG. 12 illustrates a proximal end 26 of the vaso-occlusive device 10, in accordance with still further embodiments of the disclosed inventions. The vaso-occlusive device 10 may be any of the vaso-occlusive devices 10 described with reference to FIGS. 1-9, wherein the inner coil 12 extends beyond the outer coil 14 at the proximal end 26 of the vaso-occlusive device 10, thereby providing a low profile coil for attaching to a delivery wire 28.

Figure 13:
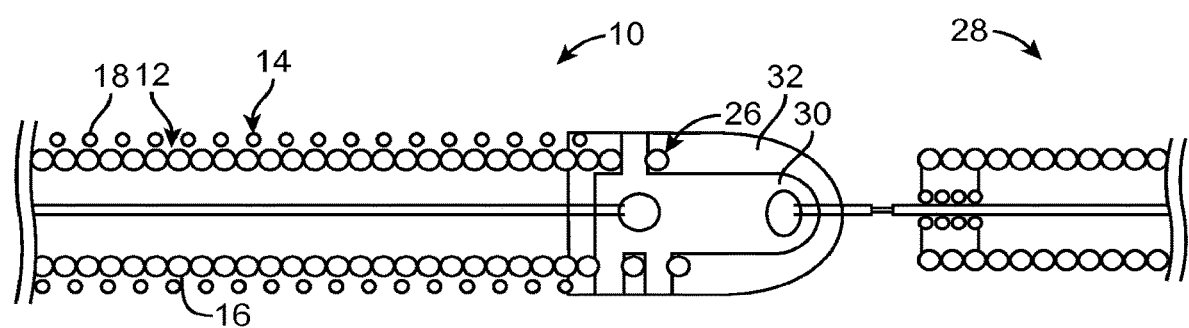
FIG. 13 is a detailed longitudinal cross-section view of the vaso-occlusive device shown in FIG. 12 connected to a delivery wire via a main junction clip.

As shown in the FIG. 13, the proximal end of the inner coil 12 is attached to the delivery wire 28 via a main junction clip 30. In particular, the proximal end of the inner coil 12 is screwed onto the main junction clip 30 within a mass 32 of glue. The mass 32 of glue has approximately the same outer diameter as the outer coil 14. In other embodiments, the attachment of the coil 12 to the delivery wire 28 may be accomplished using a weld or other suitable adhesive. Securing the outer coil 14 to only the blunt tip 24 at the distal end 22 of the vaso-occlusive device 10 (or to only one end of the inner coil 12) allows the outer coil 14 to move more easily relative to the inner coil 12, thereby providing a vaso-occlusive device 10 that is softer.

It should be appreciated that the materials for forming the coils 12, 14 of the vaso-occlusive device 10 are not be limited to the examples described previously. In any of the embodiments described herein, the material for the coils 12, 14 may be a radio-opaque material such as a metal or a polymer. Also, in other embodiments, the material for the coils 12, 14 may be rhodium, palladium, rhenium, as well as tungsten, gold, silver, tantalum, and alloys of these metals. These metals have significant radio-opacity and in their alloys may be tailored to accomplish an appropriate blend of flexibility and stiffness. They are also largely biologically inert. Also, any materials which maintain their shape despite being subjected to high stress may be used to construct the coils 12, 14.

For example, certain "super-elastic alloys" include various nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum), may be used. In further embodiments, titanium-nickel alloy known as "nitinol" may be used to form the coils 12, 14. These are very sturdy alloys which will tolerate significant flexing without deformation even when used as very small diameter wire.

In any of the embodiments described herein, the wires 16, 18 used to form the respective coils 12, 14 may have a cross-sectional dimension that is in the range of 0.00002 and 0.006 inches. The coils 12, 14 formed by the respective wires 16, 18 may have a cross-sectional dimension between 0.003 and 0.025 inches. In various embodiments, the wires 16, 18 can have any geometry, such as square, rectangle, or circle. For neurovascular applications, the diameter of the coils 12, 14 may be anywhere from 0.008 to 0.018 inches. In other embodiments, the wires 16, 18 may have other cross-sectional dimensions, and the coils 12, 14 may have other cross-sectional dimensions. In some embodiments, the wires 16, 18 for forming the coils 12, 14 should have a sufficient diameter to provide a hoop strength to the resulting vaso-occlusive coil 10 sufficient to hold the coil 10 in place within the chosen body site, lumen or cavity, without substantially distending the wall of the site and without moving from the site as a result of the repetitive fluid pulsing found in the vascular system.

In any of the embodiments described herein, the axial length of the coils 12, 14 may be in the range of 0.5 to 100 cm, and more preferably, in the range of 2.0 to 40 cm. Depending upon use, the coils 12, 14 may have 10-75 turns per centimeter, or more preferably 10-40 turns per centimeter. In other embodiments, the coils 12, 14 may have other lengths and/or other number of turns per centimeter.

Figure 14:
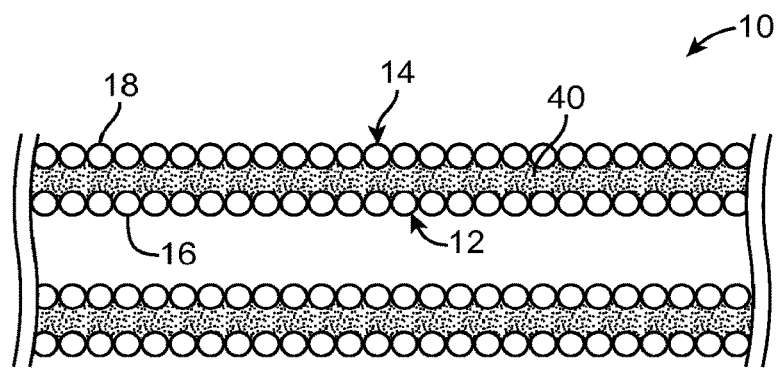
Figure 15:
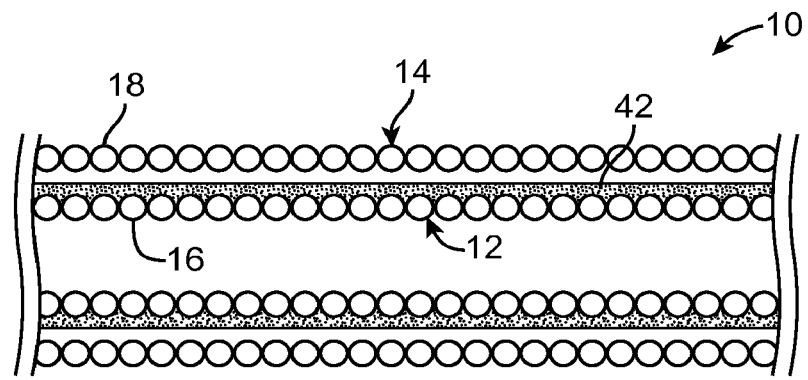
Figure 16:
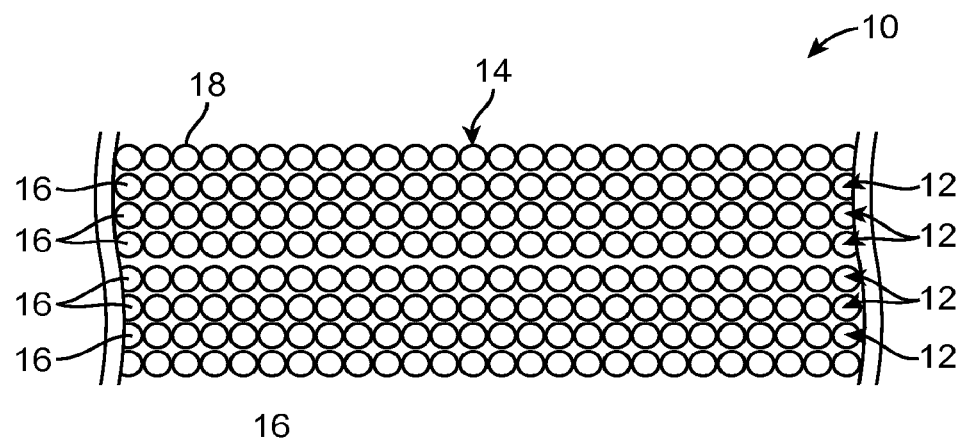

In the embodiments shown in FIGS. 14-16, the inner and outer coils 12, 14 have the same pitch, and are made from wire formed from the same material and having the same diameter. Although, the inner and outer coils 12, 14 are similar in these embodiments, they can have different pitches, and can be made from wire formed from different materials and having the different diameters.

In the embodiment shown in FIG. 14, an intermediate layer 40 is disposed between the inner and outer coils 12, 14. The intermediate layer 40 can be made from a biocompatible metal or a biocompatible and swellable polymer. In some embodiments, the intermediate layer 40 is made of material dissimilar from the materials from which the inner and outer coils 12, 14 are made. In embodiments where the intermediate layer 40 is made from a biocompatible metal, the metal corrodes and forms an oxide by-product. The oxide by-products in these embodiments or the swellable polymer in other embodiments expand against the inner and outer coils 12, 14, thereby increasing hoop strength of the vaso-occlusive device 10 and packing density of the vaso-occlusive device 10 within an aneurysm.

In the embodiment shown in FIG. 15, the outer surface of the inner coil 12 is coated with a biodegradable coating 42 such as Poly(glycolide-lactide) ("PGLA"). The coating 42 promotes adhesion between the inner and outer coils, thereby increasing strength of the vaso-occlusive device 10.

In the embodiment shown in FIG. 16, a plurality of inner coils 12 of increasing size are each disposed inside of the lumen of the outer coil 14. Each inner coil 12 is disposed immediately inside of either the outer coil 14 (the largest inner coil 12) or an inner coil (the other inner coils 12). The plurality of inner coils 12 increases the strength of the vaso-occlusive device 10. Although three inner coils 12 are shown in this embodiment, any number of inner coils 12 can be included.

Figure 17:
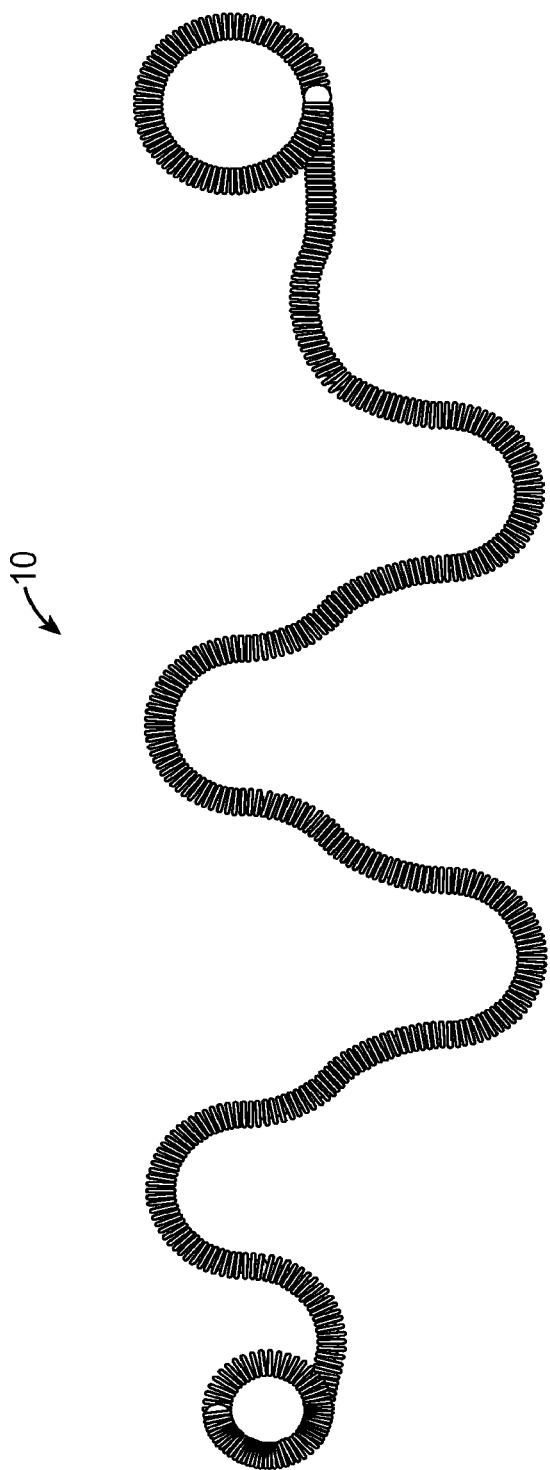
FIG. 17 is a perspective view of a vaso-occlusive device in a natural state mode, illustrating one exemplary secondary configuration.

In some embodiments, the vaso-occlusive devices 10 described herein may have the simple linear shape shown previously, or may have shapes which are more complex. FIG. 17 shows what is termed a "secondary" shape in that it is formed from the primary coil by winding the primary coil on a form of a desired shape, e.g. a mandrel, and then heat treating the so-formed shape. Various other secondary shapes may be implemented in embodiments of the vaso-occlusive device 10 described herein.

Although particular embodiments have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. An occlusive device, comprising:
   an inner coil made from an inner coil wire having a first diameter;
   an outer coil disposed at least partially around the inner coil and made from an outer coil wire having a closed pitch and a second diameter, wherein the first diameter is different from the second diameter; and
   an intermediate layer disposed between the inner coil and the outer coil;
   wherein the intermediate layer is configured to expand against the inner and outer coils such that the intermediate layer is substantially contained between the inner and outer coils; and
   wherein the occlusive device has a first hoop strength when the intermediate layer is unexpanded and a second hoop strength when the intermediate layer is expanded that is greater than the first hoop strength.

2. The occlusive device of claim 1, wherein the intermediate layer comprises a biocompatible material.

3. The occlusive device of claim 1, wherein the intermediate layer comprises a biocompatible swellable polymer.

4. The occlusive device of claim 1, wherein the second diameter is less than the first diameter.

5. The occlusive device of claim 1, wherein the inner coil wire is formed from a first material, wherein the outer coil wire is formed from a second material, and wherein the first material is different from the second material.

6. The occlusive device of claim 5, wherein the second diameter is less than the first diameter, and wherein the second material is softer than the first material.

7. The occlusive device of claim 5, wherein the inner coil has a first pitch and wherein the first pitch is different from the closed pitch of the outer coil.

8. The occlusive device of claim 7, wherein the second diameter is less than the first diameter, and wherein the second material is softer than the first material.

9. The occlusive device of claim 1, wherein the inner coil has a first pitch, and wherein the first pitch is more open than the closed pitch of the outer coil.

10. The occlusive device of claim 1, wherein the inner coil has a first pitch and the first pitch is substantially equal to the closed pitch of the outer coil.

11. The occlusive device of claim 1, wherein the inner coil extends proximally beyond the outer coil.

12. The occlusive device of claim 1, further comprising a clip, wherein the clip includes a plurality of threads configured to engage the inner coil, and wherein the clip is adapted to couple to a delivery wire.

13. A method, comprising:
placing an occlusive device within a body of a patient, the occlusive device comprising:
an inner coil made from an inner coil wire having a first diameter;
an outer coil disposed at least partially around the inner coil and made from an outer coil wire having a closed pitch and a second diameter, wherein the first diameter is different from the second diameter; and
an intermediate layer disposed between the inner coil and the outer coil;
wherein the intermediate layer is configured to expand against the inner and outer coils such that the intermediate layer is substantially contained between the inner and outer coils; and
wherein the occlusive device has a first hoop strength when the intermediate layer is unexpanded and a second hoop strength when the intermediate layer is expanded that is greater than the first hoop strength.

14. The method of claim 13, wherein the intermediate layer comprises a biocompatible swellable polymer.

15. The method of claim 14, wherein the biocompatible swellable polymer expands against the inner and outer coils thereby increasing a first packing density of the occlusive device when expanded that is greater than a second packing density of the occlusive device when unexpanded within the patient.

16. The method of claim 14, wherein the biocompatible swellable polymer expands in the presence of a body fluid within the patient.

17. The method of claim 14, wherein the biocompatible swellable polymer expands in the present of blood within the patient.

18. The method of claim 13, further comprising a clip, wherein the clip includes a plurality of threads configured to engage the inner coil, and wherein the clip is adapted to couple to a delivery wire.

* * * * *